United States Patent [19]

Bell et al.

[11] Patent Number: 5,435,937
[45] Date of Patent: Jul. 25, 1995

[54] FLUORESCENT COMPOUNDS

[75] Inventors: Colin D. Bell; John H. C. Howse, both of Cardiff, United Kingdom

[73] Assignee: Amersham International plc, United Kingdom

[21] Appl. No.: 17,674

[22] Filed: Feb. 12, 1993

[30] Foreign Application Priority Data

Feb. 14, 1992 [EP] European Pat. Off. ............ 92301249

[51] Int. Cl.⁶ .................... C09K 11/04; C09K 11/06; C07F 9/535
[52] U.S. Cl. ........................... 252/301.18; 252/301.17; 252/301.34; 252/301.35; 252/625; 252/646; 534/11; 534/12; 534/15; 534/16; 556/26; 556/30; 556/31
[58] Field of Search ....................... 252/301.18, 301.17, 252/301.34, 301.35, 625, 644, 646; 534/11, 12, 15, 16; 556/26, 30, 31

[56] References Cited

U.S. PATENT DOCUMENTS

| | | | |
|---|---|---|---|
| 3,377,292 | 4/1968 | Halverson | 252/301.18 |
| 3,398,099 | 8/1968 | Kleinerman | 252/301.18 |
| 3,440,173 | 4/1969 | Hovey et al. | 252/301.18 |
| 3,539,941 | 11/1970 | Halverson | . |
| 4,037,172 | 7/1977 | Filipescu et al. | 252/301.18 |
| 4,997,597 | 3/1991 | Clough et al. | 252/646 |
| 5,158,703 | 10/1992 | Takuma et al. | 252/301.35 |

FOREIGN PATENT DOCUMENTS

2242908 10/1991 United Kingdom .
WO89/05844 6/1989 WIPO .

OTHER PUBLICATIONS

Sinha, A. P. B., *Spectroscopy in Inorganic Chemistry,* edited by C. N. R. Rao and John R. Ferraro, vol. 2, Academic Press, 1971—History of Congress, Catalogue No. 77-117102. (Month unknown).
Kallistratos, G., *Chimika Chronika, New Series,* 11, 249-266 (1982). (Month unknown).
Reid et al., *Journal of the American Chemical Society,* 72, 2948-2952 (1950). (Month unknown).
Baldwin et al., *Journal of the American Chemical Society,* 83 4466-4467 (1961). (Month unknown).
Harger et al., *Tetrahedron,* 38(10) 1511-1515 (1982). (Month unknown).

*Primary Examiner*—Prince Willis, Jr.
*Assistant Examiner*—Alan D. Diamond
*Attorney, Agent, or Firm*—Wenderoth, Lind & Ponack

[57] ABSTRACT

Novel compounds obtainable by reacting together an imido-reagent such as diphenylphosphonimidotriphenylphosphorane) with a chelate of a transition or lanthanide or actinide metal, such as tris(dibenzoylmethide) europium III, has the property of fluorescing in UV radiation. The invention includes solid polymer bodies containing such compounds, or chelates of transition or lanthanide or actinide metals generally, the bodies having the property of emitting light by virtue of internally generated, e.g. by tritium ionising radiation. The body is preferably of polystyrene formed by polymerising the monomer in the presence of the compound or metal chelate.

28 Claims, 10 Drawing Sheets

FLUORESCENT COMPOUNDS

This invention concerns polymer bodies which are light-emitting by virtue of containing a transition or lanthanide or actinide metal chelate or other complex. For the most part, the energy for light emission is provided by internal radioactivity, e.g. by using a tritiated polymer. In the course of the work leading to this invention, novel compounds based on certain metal chelates have been identified as having outstanding fluorescent properties. These compounds, and polymer bodies containing them, also form part of this invention. All these compounds and chelates are fluorescent, in the sense that they emit light or other relatively long wavelength electromagnetic radiation, on being subjected to UV or other relatively short wavelength electromagnetic radiation, including ionising radiation from radioactive decay. It is surprising that the compounds and chelates show high efficiency of light output and good stability in the presence of ionising radiation.

British patent specification 2242908 describes tritiated light emitting polymer compositions, containing one or more organic fluors linked to the polymer in some way, for example as a result of having been dissolved in the monomer prior to polymerisation. The polymer compositions can be made transparent or translucent so that useful light is emitted from the entire volume of the polymer. Such compositions have other advantages: they are easily fabricated and shaped; the tritium is present in combined form and so is not released by accidental damage (as would for example be the case with a glass envelope containing gaseous tritium); when performance falls off, the composition is easily replaced and recycled. But using the organic fluors described, the generation of light from radioactive decay is not as efficient as may be desired. As a result, the polymer composition may be subject to radiation damage from the high concentrations of tritium needed to generate bright light.

Rare earth chelates having the property of fluorescing in UV radiation are well known. A. P. B. Sinha (Spectroscopy in Inorganic Chemistry edited by C. N. R. Rao and John R. Ferraro, Vol. 2, Academic Press 1971—History of Congress Catalogue No. 77-117102) describes several classes of rare earth chelates with various monodentate and bidentate ligands. The mechanism of fluorescence is also described. The first step involves the absorption of energy by the organic part of the chelate leading to its excitation from a ground state singlet to an excited singlet. The excited molecule can then go over to a triplet state in which energy can be transferred to a central rare earth metal ion. The excited metal ion can then undergo a radiative transition resulting in the characteristic line emission of the ion (ion fluorescence). All these steps take place in competitions with other nonradiative steps. For efficient fluorescence, it is necessary that the transition metal ion have a resonant frequency which is close to, but slightly lower than, the excited triplet frequency of the chelating group. This ensures that the probability of triplet-to-resonance level transition is high. Other complexes of Group IIIA metals and rare earth and lanthanide metals with aromatic complexing agents have been described by G. Kallistratos (Chimika Chronika, New Series, 11, 249-266, 1982). For example, this reference describes the Eu 3+, Tb 3+ and U 3+ complexes of diphenyl-phosphonimido-triphenyl-phosphoran.

In one aspect this invention provides a solid body comprising an organic polymer or a mixture of organic and inorganic polymer, together with a chelate of a transition or lanthanide or actinide metal, the body having the property of emitting light by virtue of internally generated ionising radiation. Preferably the polymer is radioactively labelled so that the radioactive decay provides the ionising radiation.

The metal chelate may be the same as or similar to the known classes of metal chelate referred to above. However, it needs to have a number of special properties not always possessed by the known fluorescers:

It needs to be capable of fluorescing under the impact of UV or other electromagnetic radiation, not only in pure form but also in dispersion or solution in an organic monomer or polymer.

It is preferably soluble in the monomer or monomer mix used to form the polymer body. A solubility of at least 10% by weight is generally preferred. The metal chelate should preferably remain soluble as the monomer polymerises.

The presence of the metal chelate should preferably not inhibit polymerisation of the monomer to a transparent wholly or substantially colourless polymer.

Up to the present time a scintillant has normally been regarded as consisting of a solvent plus one, two or three solutes. The solute with the fluorescence level highest in energy is called the primary solute or scintillator and the second and third solutes are known and act as wavelength shifters. The scintillation process has thus been seen as involving the following steps: absorption of nuclear radiation by the solvent with the formation of a solvent excited state; energy transfer from the solvent to a primary scintillant followed by fluorescence emission; absorption and re-emission by secondary and possibly tertiary scintillants to shift the final emitted light to the desired wave-length.

It has surprisingly been discovered that the chelates of the transition metals particularly those of the rare earths, can act as primary scintillants, such that the nuclear radiation energy adsorbed by the solvent (polymer) is transferred to the chelate or chelates and only emitted at the final desired wavelength, this process being achieved without the use of secondary or tertiary scintillants or wave-shifters. These chelates have thus minimised energy losses and give rise to more efficient light output. The metal chelates often have very narrow emission spectral bands, which can be designed to be at particular wavelengths, thus enabling photodiodes to be used at high efficiency.

In principle, any metal ion having an unfilled inner electron shell, that is to say almost any transition or lanthanide or actinide metal ion, can be used as the basis of the fluorescent chelate. In practice, a metal ion having a convenient emission frequency, and a convenient resonant frequency, and an efficient transition between the two, is most usually chosen. The most usual are the lanthanide metal ions Sm 3+, Eu 3+, Tb 3+, Dy 3+, Yb 3+, Lu 3+, Gd 2+, Eu 2+, and the actinide metal ions U 3+ and $UO_2$ 3+.

The chelating or complexing groups are chosen to have a triplet energy level similar to but slightly higher than the resonant energy level of the chosen metal ion. Known chelates, including those described in the abovementioned references are likely to be suitable, including those based on diketone and triketone chelating moieties. A preferred chelating group has the formula

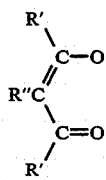

where R' may be the same or different at different parts of the molecule and each R" and R' is an aromatic or heterocyclic ring structure which may be substituted or hydrocarbon or fluorocarbon or R" is hydrogen. The identity of R" can be used to modify the triplet energy and may affect light emission. R" can also be made co-polymerisable with a monomer, e.g. styrene.

In the compound described in Example a) below, R' is t-butyl and R" is hydrogen. Metal chelates may have up to four, typically three, of such groups surrounding the metal ion.

Examples of metal chelates useful in this invention are:

a) Terbium (3+) (dipivaloylmethide)3, otherwise known as terbium tris(2,2,6,6-tetramethyl-3,5-heptanedionato) chelate, commercially available from Strem Chemicals.

b) The di- and tri-pyrazolyl borate and the di- and tri-pyrazolyl-N-oxide borate adducts of a).

c) Europium (3+) (2-naphthyl trifluoroacetyl acetonate)4 d) Uranyl (2-naphthyl trifluoroacetyl acetonate)4. This material emits strongly in the yellow part of the spectrum when cooled to about $-50°$ C.

e) The dipyridyl and dipyridyl-N-oxide adducts of c) and d).

f) A family of novel compounds derived from metal chelates as in a) to e) above has shown interesting fluorescent properties and is included within the scope of the invention.

In this aspect the invention provides a compound that results from reacting together an imido-reactant of formula

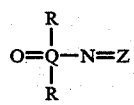

where Q may the same or different at different parts of the molecule and is P, As or Sb, and R may be the same or different at different parts of the molecule and each R is an aromatic or heterocyclic ring structure which may be substituted or unsubstituted, provided that one group R may alternatively be a co-polymerisable group, and Z is either $QR_3$ or an oligophosphoranyl group (an organophosphoranyl group with two or more P atoms), with a chelate of a transition or lanthanide or actinide metal ion to produce a product which has the property of fluorescing in UV radiation.

These compounds are expected to have the formula

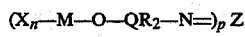

or $$X_n-M(-O-QR_2-N=Z)_s$$

where M is the transition or lanthanide or actinide metal ion, such as those described above,
X is a chelating group,
n is 1 to 4,
p is 1 to 4, and
s is 1 to 4 preferably 1 or 2.

In the above structures, Q may be Sb or As or P, the latter being preferred. At least four of the five groups R should be of aromatic or heterocyclic character, the following being examples: phenyl; p-tolyl; 2,4-dimethylphenyl; p-tertiary butyl phenyl; 1-naphthyl; 2-naphthyl; 4-pyridyl; 4-quinolyl.

Z may be an oligophosphoranyl group, e.g. of the formula:

$$Ar_1-P-[(Alk-P-Ar)_m-Alk-P-Ar_2]_q$$

where Ar is aryl preferably phenyl, Alk is alkene preferably $-C_2H_4-$, l, m and q are small integers such that $1+q$ is 3, these compounds being of the kind commercially available as:

Diphos—$Ph_2PC_2H_4PPh_2$.
Triphos—$Ph_2PC_2H_4P(Ph)C_2H_4PPh_2$.
Tetraphos I—$Ph_2PC_2H_4P(Ph)C_2H_4PPhC_2H_4PPh_2$.
Tetraphos II—$P(C_2H_4PPh_2)_3$.

(See JACS 93:17 Aug. 25, 1971; 4158–4166). For example, a compound according to the invention based on Diphos would have the formula:

$$X_n-M-O-P(Ph)_2-N=P(Ph)_2-C_2H_4-P(Ph)_2$$
$$=N-P(Ph)_2-O-M-X_n$$

where Ph is phenyl.

Alternatively, one of the groups R may be a co-polymerisable group, that is to say a group capable of joining in a polymerisation reaction with a monomer with which the compound is mixed. Examples are carboxylic and sulphonic acid groups, and ethylenically unsaturated hydrocarbon groups such as allyl and p-styryl. A preferred imido reagent has the formula

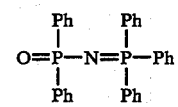

where Ph is phenyl.

Preparation of the compounds of this invention is straightforward. Transition metal chelates such as those described by A. P. B. Sinha (reference above) are well known. Some are commercially available. General methods of preparation are described by Reid and Calvin (Journal of the American Chemical Society, 72 (1950), 2948–2952). Imido reagents are known materials (see the Kallistratos reference above) whose preparation is described by R. A. Baldwin and R. M. Washburn (Journal of the American Chemical Society, 83, pages 4466–4467, 1961) and M. J. P. Harger and S. Westlake (Tetrahedron, 38, No. 10, pages 1511–1515, 1982). To prepare compounds according to the present invention, the chosen metal chelate and the chosen imido-reactant may be heated together in molar quantities defined by the formulae above at a melting temperature of 200° C. for one hour. More preferably, appropriate molar quantities of the two reactants are heated together in a refluxing organic solvent. The inventors have found trimethylpentane when s is 1 and toluene when s is 2 to be convenient. If the starting metal chelate is insoluble, progress of the reaction can be monitored by noting that the refluxing solution clears. On cooling, the desired product crystallises out in easily recoverable form.

This aspect of the invention is not restricted to compounds prepared by this route, and other preparative methods are possible. For example, one molar part of a complex of the metal ion with the imido-reactant may be heated with generally 2-4 molar parts of the chelating moiety so as to form the desired compound.

The compounds, individually, have the property of fluorescing, in the visible or infra-red region depending on the metal ion chosen, when subjected to UV or other energetic radiation. This property may be exploited in various ways. For example, the compound may be applied as a coating on a glass vessel or on glass beads, and these may be maintained in the presence of a radioactive gas such as tritium or xenon-133 or krypton-85.

The compounds, in combination, may act in a less well known manner. In certain circumstances the energy collected by the metal ion of one structure will not be emitted by that ion but will be transferred most efficiently, by so-called radiationless transfer, to a second different metal ion (chelated). This phenomenon, known as 'ion to ion transfer' can be made very efficient by careful selection of the two metal ion structures. For example, trivalent gadolinium structures do not usually emit light even in isolation but, in combination with known fluorescent lanthanide chelates, they prove to be very efficient energy collectors. Such metal ion chelate pairs can be of greater efficiency than any one chelate on its own.

The compounds of this invention are particularly useful in polymer compositions. Thus in another aspect the invention provides a solid body comprising an organic polymer or a mixture of organic and inorganic polymer together with at least one compound as described above, the body being capable of emitting light when subjected to a flux of electromagnetic radiation. Preferably, the flux of electromagnetic radiation is generated internally by radioactivity in the solid body.

Thus, either the polymer or the metal chelate (which term is hereafter used to include novel compounds of this invention) may be radio-labelled, preferably with tritium. In these compositions, the metal chelates act as scintillants, either alone or in conjunction with conventional organic scintillants.

Polymers labelled with tritium are well known, and are most conveniently prepared by labelling a monomer or co-monomer with tritium prior to polymerisation. The polymer should preferably be clear for maximum efficiency at the wavelength of the emitted light, and should preferably be resistant to damage by self-irradiation (E. A. Evans, Tritium and Its Compounds, 2nd Edition, Butterworths, London 1974 pages 720-721). On these grounds, polymers of vinyl-aromatic hydrocarbons, such as styrene and vinyltoluene, are preferred. A $G_s$ (scission) value of 0.04 is quoted for irradiation of polymethylstyrene and a $G_x$ (crosslinking) value of 0.02 which is much less than for other known polymers, see Polymer Photophysics and Photochemistry by J. Guillet Pub. Cambridge University Press, 1985 page 353 et seq. Some or all of the protium hydrogen in the polymer and/or in the metal chelate may be replaced by deuterium. Additional stability is however conferred on the composition by the presence of the metal chelates, by virtue of their conversion of beta radiation energy into light, reducing the proportion of energy available for self-irradiation of the polymer.

The extent of tritium labelling is a compromise between several factors. By incorporating 2 atoms of tritium per monomer molecule, it is possible to achieve activities of 600 Ci/g. Such monomers may be diluted with non-radioactive monomer, or the monomer prepared using tritium-hydrogen mixtures in the tritiation/hydrogenation step, to achieve the overall specific radioactivity required. Activities below about 100 mCi/g are rather unlikely to be useful as illuminating devices but do have a use as light sources for calibration. As the tritium labelled polymer is a relatively expensive material, it will generally be preferred to use the minimum required to achieve the desired light output. All polymers labelled with radioisotopes including polystyrene suffer from radiation damage, and at high levels of activity this may lead to darkening with loss of light output, and eventually to embrittlement and degradation. Labelling to an activity of from 25 nanocuries/gram to 100 Ci/g, particularly 50 nanocuries/gram to 5 curies/gram, of composition may be appropriate in many cases, with activities towards the lower end of that range where a service life of more than five years is required.

Tritiated vinyl aromatic monomers may be made by the catalytic partial reduction by tritium of substituted acetylenes. For the purpose of this invention, reduction is carried out with tritium-hydrogen or tritium-deuterium mixtures up to 100 per cent isotopic abundance of tritium as required, preferably in the presence of a platinum or palladium catalyst or other suitable hydrogenation catalyst. The catalyst chosen should not contain volatile components such as quinoline and should not be adversely affected by monomer stabilisers. After the reduction it is preferable to remove by filtration or by distillation any catalyst from the tritiated monomer. It is also preferable to dilute the tritiated monomer with non-radioactive monomer(s) which have been purified either by distillation or by passage through a column of neutral alumina. Vinyl aromatic monomers which are tritium labelled on the aromatic ring are also known and may be used.

The concentration of the metal chelate should be enough to efficiently convert the beta-radiation into visible light, but not so great as to inhibit polymerisation of the monomer mix or to substantially harm the properties of the polymer. While optimum concentrations may vary depending on the nature of the polymer, the extent of tritium labelling, and the nature of the scintillant, suitable concentrations are likely to lie in the range 1 μg to 500 mg, preferably 10-200 mg of total scintillant per ml of polymer. The concentration of scintillants are optimised for the light output required but too high a concentration will result in self-absorption of the light and thus reduce the efficiency—see Design Principles of Fluoresence Radiation Converters by G. Keil in *Nuclear Instruments and Methods* 87, 111-123 (1970).

A cross-linking agent may be included in the monomer mix and may be beneficial in increasing light output, as discussed below. For example, with a vinyl aromatic system, up to 50 g/l of divinylbenzene may be useful.

These light-emitting polymer compositions may be made by providing a reaction mix comprising at least one polymerisable organic monomer, preferably a vinylaromatic hydrocarbon, labelled with tritium, and at least one metal chelate scintillant, and subjecting the reaction mix to polymerisation conditions. The scintillant is preferably present in solution in the monomer. Transition metal chelates are often sparingly soluble in vinylaromatic monomers; a preferred feature of adducts such as the aromatic imido-moiety is to render the compounds of this invention highly soluble. Preferably, polymerisation of the monomer or monomers is effected by heat in the presence or absence of free-radical polymerisation initiators and in the substantial absence of oxygen. When the polymerisation reaction is exothermic, careful temperature control of the reaction mix may be needed to avoid thermal decomposition of the organic scintillators. The reaction mix may be shaped prior to polymerisation to generate plastic sheets of desired thickness, rods, filaments, microbeads, capillary tubing, or other desired shapes. After polymerisation, the solid products can also be cut and shaped as desired. These shapes may be "silvered" in known manner to increase directional light output. Thus the body may be in the shape of cylinder with the curved surface made internally reflecting, or of a chord of a cylinder with the curved surface and the ends made internally reflecting.

Upon polymerisation of the monomer mix, the light emitted by the composition increases, to an extent that is dependent on various factors. Use of purer reagents; increasing the hardness and/or rigidity of the product (and for this reason a cross-linking agent may be beneficial); cooling the product, stretching the product or otherwise inducing crystallisation; all these steps may increase light output from a given composition.

The light emitting compositions of this invention are useful wherever a continuous or intermittent independent light source is required and power lines or batteries cannot conveniently be provided, or as a detector of radiation. Some examples are:

Production of electricity by combination with photocells.

In liquid scintillation compositions as well as polymers, e.g. for liquid scintillation beta measurements.

In radiation, e.g. X-ray, visualisation screens where the efficiency of the new phosphors may be used to reduce exposure and/or improve definition.

Light sources for signs, gun-sights, markers on instruments.

Large light sources on airfields and other situations where remote lighting may be required (see also G. Foldiak in Industrial Application of Radioisotopes, Pub. Elsevier 1986, p.386 et seq. and A Novel Light-Collection System for Segmented Scintillation-Counter Calorimeters, V. Eckardt, R. Kalbach, A. Manz, K. P. Pretzl, N. Schmitz and D. Vranic, *Nuclear Instruments and Methods*, 155, 389–398 (1978).

Reference is directed to the accompanying drawings in which.

Figure 1:
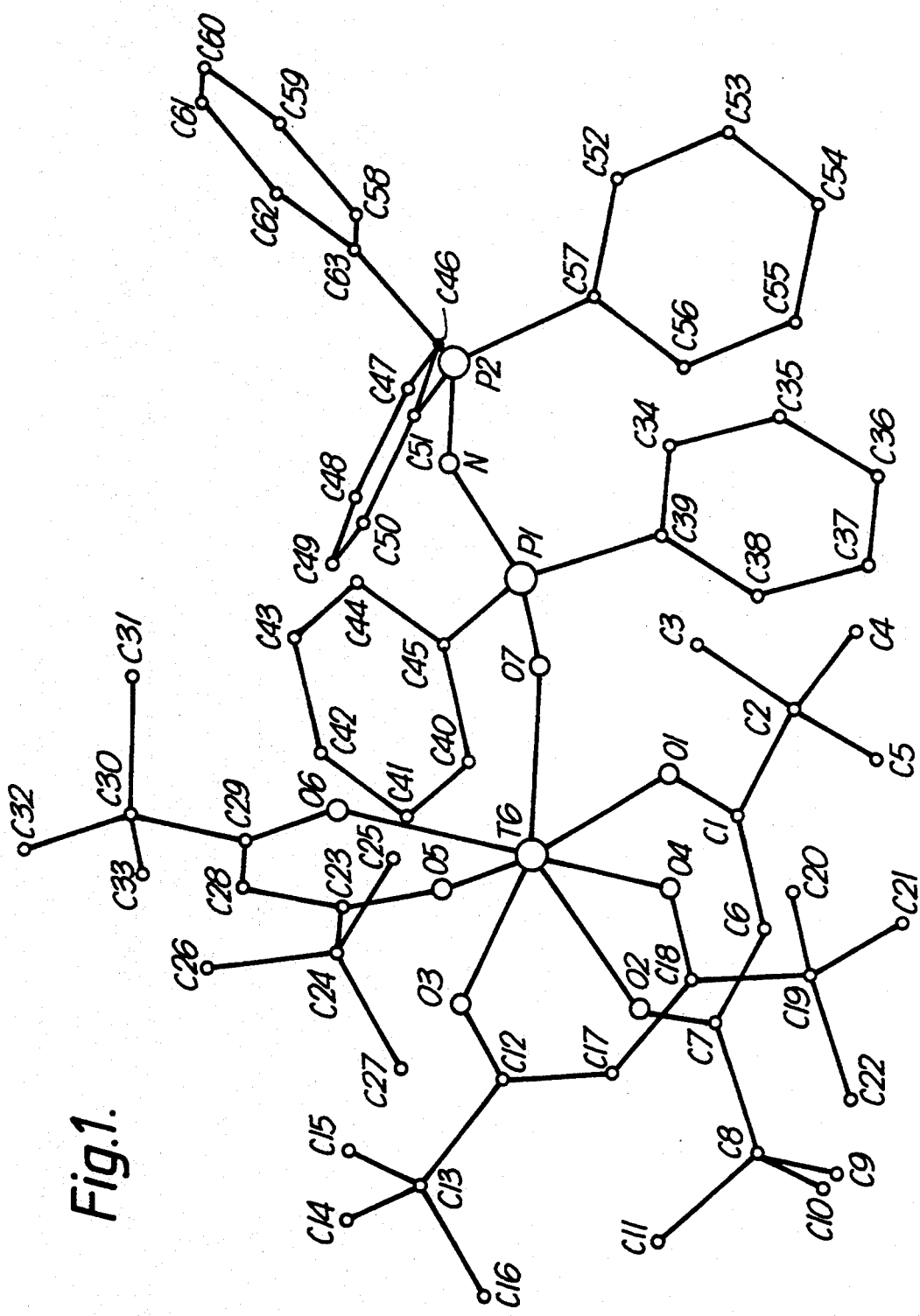
FIG. 1 is a structure, obtained by X-ray crystallography, of the compound tris(2,2,6,6-tetramethyl-3,5-heptanedionato)terbium III-diphenylphosphonimido-triphenyl phosphorane.

The following examples illustrate the invention.

EXAMPLE 1

Tris(2,2,6,6,tetramethyl-3,5-heptanedionato)terbium III-diphenyl-phosphonimidotriphenyl phosphorane (ALP-1)

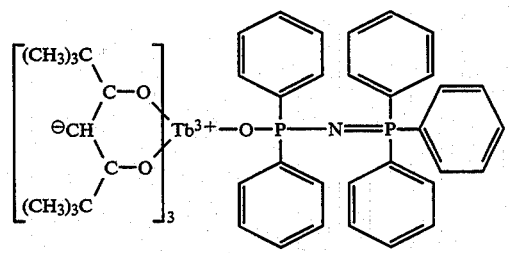

Tris(2,2,6,6-tetramethyl-3,5-heptanedionato)terbium III+ (2) was purchased from Strem Chemicals Inc.

Diphenyl-phosphonimido-triphenyl phosphorane (3) was prepared by a method given in the references quoted above. Diphenyl-phosphinic acid chloride (68 g) and sodium azide (30 g) were stirred in dried acetonitrile (380 ml) for 64 hours. Diphenylphosphinic azide precipitated out of solution, was filtered off and washed with acetonitrile and dried to yield 72.3 g.

24.1 g (100 mM) of the diphenylphosphinic azide was dissolved in dry diethyl ether (50 ml) to yield 70 ml solution. Triphenylphosphine (26 g 100 mM) was dissolved in diethyl ether (dried 160 ml) and the two reagents mixed and refluxed in a 500 ml flask fitted with a reflux condenser.

The precipitated material was filtered off, washed with a) ether, b) dilute ammonia solution (10 ml of 2N ammonia diluted to 100 ml), and c) water (5×100 ml), and dried at room temperature under vacuum to yield 36.31 g (76% of theory) of (3).

1 mM of (2) was mixed with 1 mM of (3) in a total of 5 ml trimethyl pentane, and the mixture heated to reflux until a clear solution was obtained (about 1 hour). The solution was allowed to cool yielding (ALP-1) as a crystalline solid in nearly quantitative yield.

X-ray crystallographic examination of single crystals of the product ($C_{63}H_{82}O_7P_2NTb$; M.W. 1886.166) gave rise to the structure shown in FIG. 1. Thermal analysis by differential scanning calorimeter gave a melting point of 169.8° C.

EXAMPLE 2

Light emitting polymer preparation using (1)

Reduction of intermediate to yield diluted tritiated monomer

Phenylacetylene (1 mM 100 mg) was reduced with 60 curies tritium gas in the presence of Pdc catalyst—(reference see Example 5, 1 ml solution pumped to dryness under vacuum) then styrene (10 ml without the stabiliser removed) added along with a magnetic stirrer. The phenylacetylene was quantitatively reduced to tritiated styrene without there being any significant further reduction of the styrene to ethyl benzene.

This produced about 10 milliliters or grams of tritiated styrene at 6 curies/gram or milliliter—still containing Pdc catalyst and polymerisation inhibitor. The tritiated styrene was removed from the catalyst, polymerisation inhibitor and any other contaminants by vacuum distillation and the resulting pure tritiated styrene added as required to (ALP-1) undiluted or diluted to give a final solution of (ALP-1) in the tritiated monomer.

Polymerisation to yield L.E.P.

A solution of polymerisation catalyst (AZBN) was added to yield a final catalyst concentration of 0.1 milligrams per milliliter. The solution was then flushed with argon/methane to minimise oxygen content which tends to quench light emission, and the container was sealed and the solution polymerised at 60° C. for 16 hours.

The polymer was allowed to cool to room temperature to yield a virtually colourless high clarity polymer with a bright yellow/green (545 nanometers) light emission.

A considerable increase in light output was observed as the monomer polymerised to completion.

Polymer shaping and applying reflective coatings

The product may then be further shaped as it is a thermoplastic to emit its light optimally in one plane and further efficiency of emission may be obtained by applying a reflective metal coating to parts of the shaped product. For the tests described below, the body was formed in the shape of a chord of a cylinder with the curved surface and the ends made internally reflecting by being coated with aluminium metal.

Figure 2:
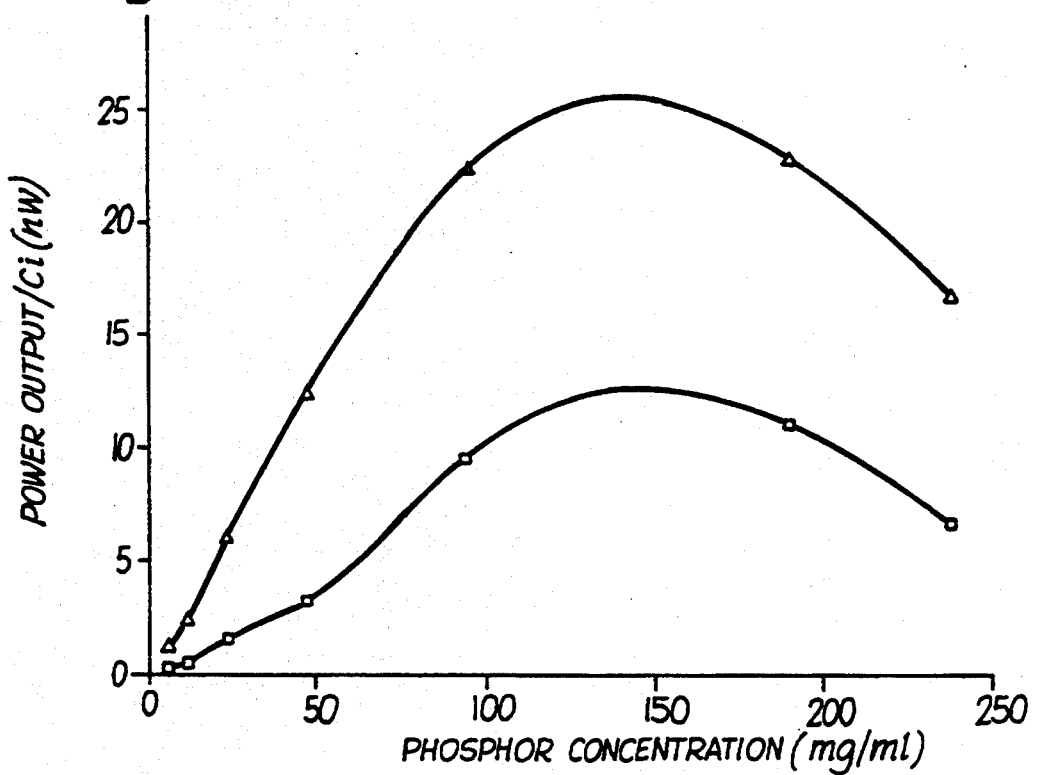
FIGS. 2 and 3 are graphs of power output against phosphor concentration at two different polymer tritium concentrations.

FIG. 2 is a graph of power output (expressed in nW/Ci) against phosphor concentration at a fixed polymer tritium concentration of 6.06 Ci/g. The upper curve of the graph was obtained in an experiment in which the light emitting body was "silvered" and optically linked to a photodiode. The lower graph was obtained in an experiment in which these steps were omitted.

Figure 3:
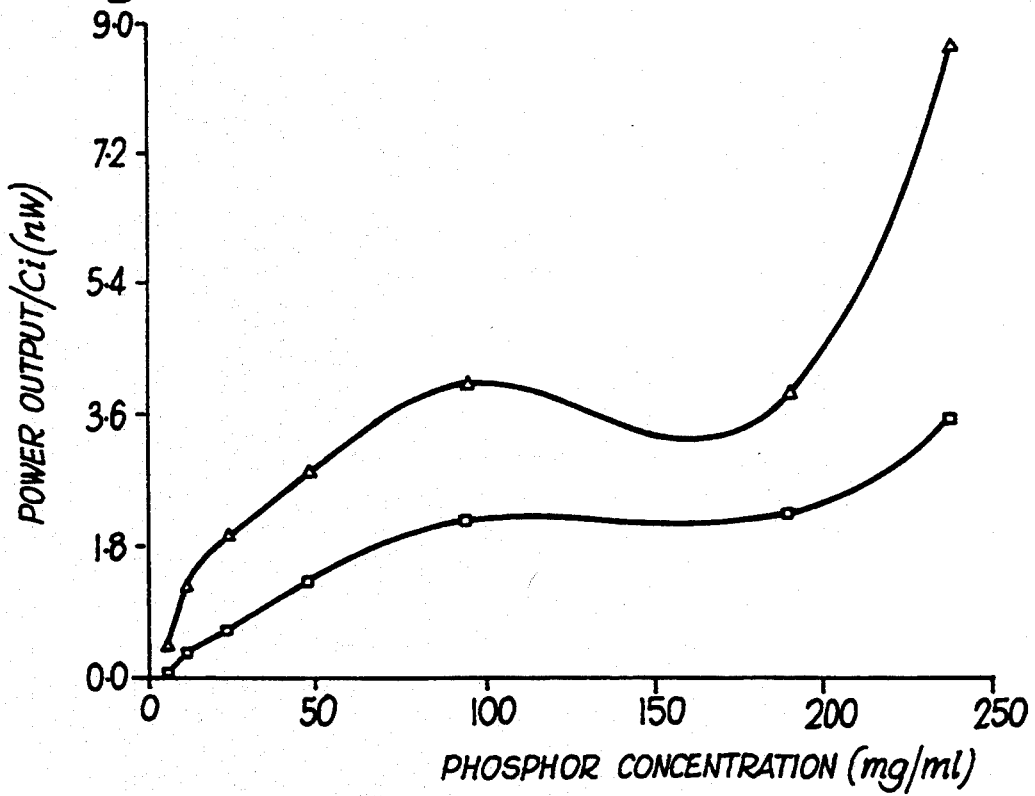

FIG. 3 is a corresponding graph, in which the polymer tritium concentration was 0.606 Ci/g, with the upper graph representing a light emitting body which is linked and "silvered", and the lower graph obtained in an experiment in which these steps were omitted.

Figure 4:
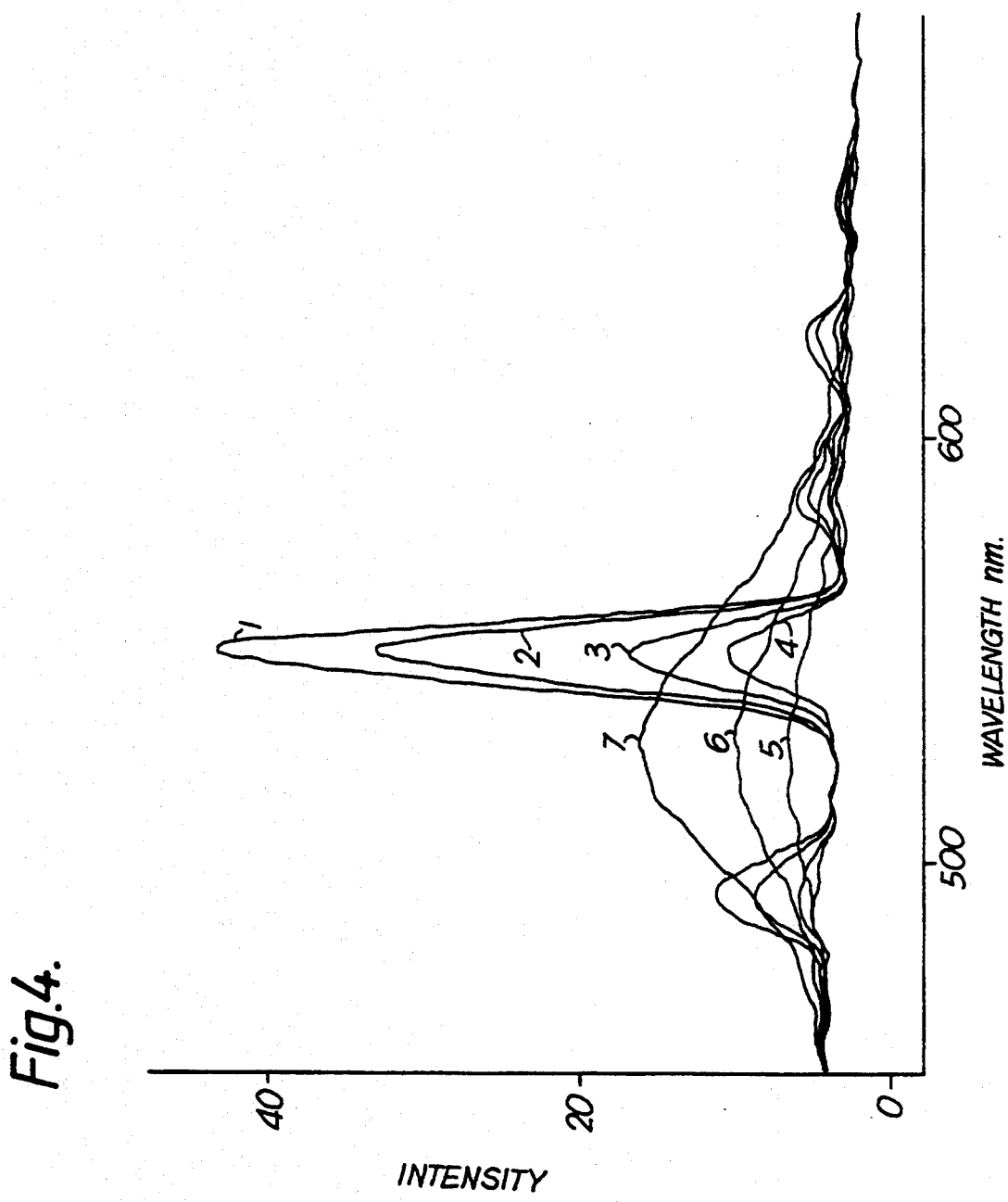
FIG. 4 is a graph of light emission intensity against wavelength for different light emitting sources.

FIG. 4 is a graph of emitted light intensity against wavelength for compositions having a polymer tritium concentration of 6.06 Ci/g and various phosphor concentrations. More specifically, it is a comparison of polymer source with MB Microtec gas source. Polymer radioactive concentration is 6.06 Ci/g. Curves 1, 2, 3 and 4 were obtained with different concentrations of phosphor. Curves 5, 6 and 7 are included for comparison, and were obtained using a commercially obtainable source containing tritium gas in a glass vessel coated with zinc sulphide scintillant. The concentrations are as follows: 1) 189.6 6mg phosphor; 2) 94.8 mg phosphor; 3) 47.4 mg phosphor; 4) 23.7 mg phosphor; 5) 1 MB Microtec source (0.5 Ci); 6) 2 MB Microtec sources (1.0 Ci); and 7) 3 MB Microtec sources (1.5 Ci). The fluorescent emission of the phosphor of this invention is strikingly monochromatic at 545 nm, and the peak intensity at this wavelength is much higher than obtainable from the commercially available sources.

EXAMPLE 3

Preparation of Europium (3+) tetra (naphthalene trifluoroacetylacetonate) bipyridyl (Eu(NTFA)$_4$ bipyr)

Naphthalene trifluoroacetylacetonate (ex Lambda Probes & Diagnostics (Austria). 4.7 millimoles (1.25 grams) were dissolved in ethanol (10 ml) and Europium trichloride (1.04 millimoles, 1.04 grams) dissolved in ethanol (5 ml) was added. The combined solutions were heated at 65° C. for 30 minutes.

Bipyridyl (2 millimoles, 352 milligrams) dissolved in ethanol (5 ml) was then added and the solution maintained at 65° C. for 30 minutes.

The total volume was then reduced to 10 milliliters, neutralised with sodium hydroxide solution and stored overnight at +2° C.

The resultant precipitate was filtered off, washed with ethanol:water (7:3) (5 ml) and dried at 100° C. under vacuum.

EXAMPLE 4

Terbium (3+) (2,2,6,6-tetramethyl-3,5-heptanedionato) chelate was purchased from Strem Chemicals. Methods of preparing the pyrazolyl borates are described by E. Trofimenko J.A.C.S. 89: 13/ Jun. 21, 1967. The tri-pyrazolyl borate adduct was prepared by heating stoichiometric amounts of the chelate and the pyrazolyl borate in acetone to dissolution, driving off the acetone and melting the residue to a clear melt at minimum temperature. After cooling, the solid was crushed to a powder and any residual solvent pumped off under vacuum at room temperature.

EXAMPLE 5

Formulations using lanthanide chelates to produce a light emitting polymer emitting at 614 mµ or 546 mµ

Phenylacetylene (3 mmoles, 290 µl) dissolved in styrene—d$_8$ (5 ml) were added to the dried homogeneous Pdc catalyst obtained from 4 ml of catalyst solution (Brunet+Caubert, J. Org. Chem., 1984, 49, 4058–4060).

The above solution was stirred with 200 curies tritium gas. The phenylacetylene is quantitatively reduced to tritiated styrene without there being any significant further reduction of the styrene to ethyl benzene.

This tritiated styrene dissolved in the fully deuterated styrene—d$_8$ is removed from the catalyst, polymerisation inhibitor and other contaminants by vacuum distillation.

1 ml aliquots of this material were added to the following:

| | | |
|---|---|---|
| a) | Terbium [DPM]$_3$ P$_{g3}$B (see Example 4) | 21.1 mg |
| | Butyl PBD (primary scintillant) | 100 mg |
| | Divinyl benzene (cross-linker) | 10 microlitres |
| | AZBN catalyst for polymerisation | 1 mg |
| | —1.5 curies | |
| b) | Terbium [DPM]$_3$ P$_{g3}$B] (different batch to a) | 20 mg |
| | Divinyl benzene | 20 microlitres |
| | AZBN | 1 mg |
| | —8.0 curies | |
| c) | Europium NTFA bipyridyl (see Example 3) | 20 mg |
| | Butyl PBD | 100 mg |
| | Divinyl benzene | 20 microlitres |
| | Triphenyl styryl lead | 5 mg |
| | —8.0 curies | |

The volume of each aliquot was about 1.1 ml. The tritium activity was as stated, achieved by use of different specific activity tritium gas.

All three solutions were sealed under nitrogen, the containers sealed and the solutions polymerised at 60° C. for 16 hours.

The polymer was allowed to cool to room temperature to yield clear polymer pieces.

The emission of each piece was measured after shaping to a uniform size and shape in a mould and partially silvering by vapour deposition to guide the light out of one surface.

Figure 6:
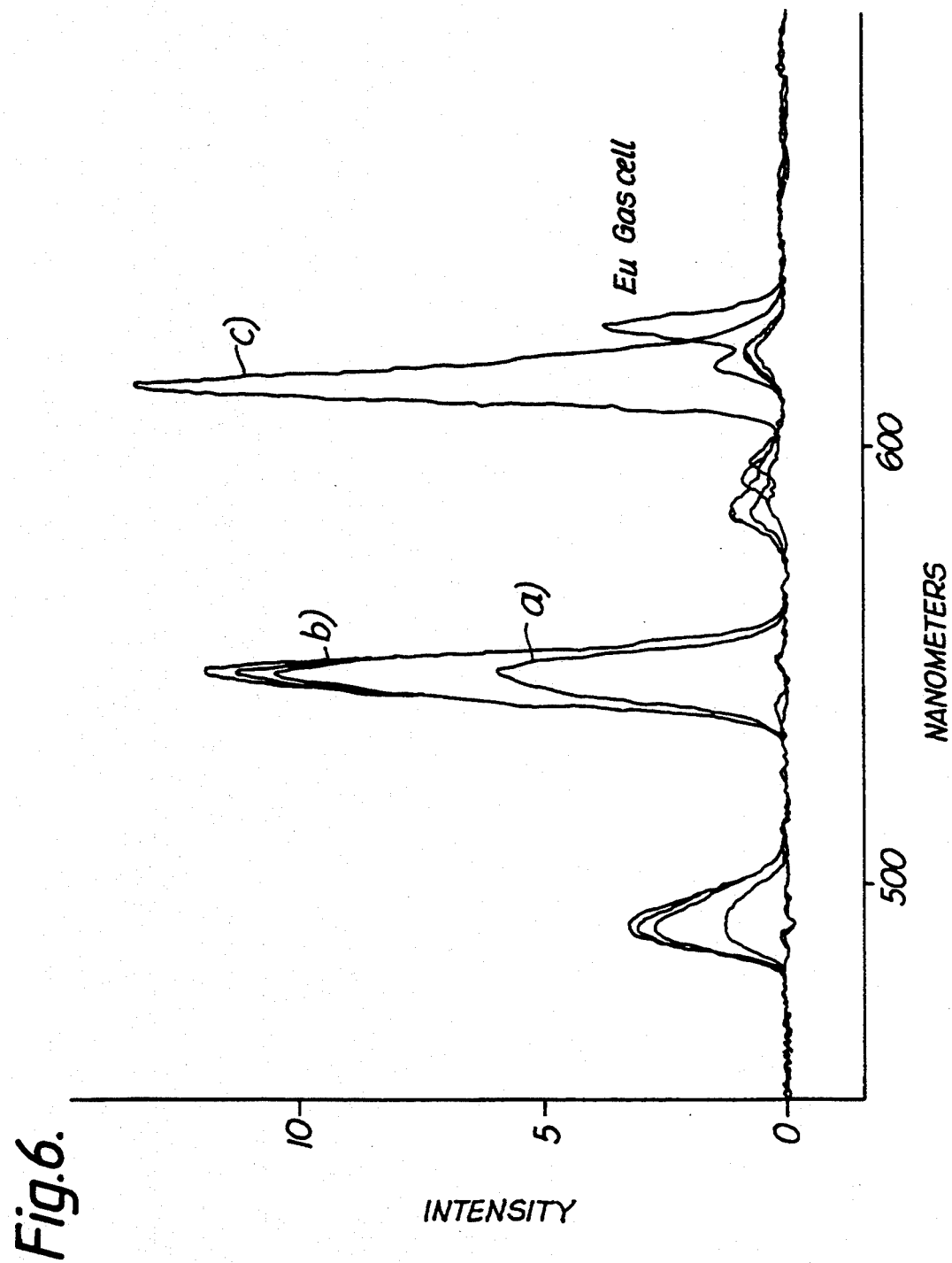
FIG. 6 is a graph of light emission intensity against wavelength for the formulations of Example 5.

The emission spectra (see FIG. 6), shows that the europium chelate containing polymer piece emits light at ~614 millimicron (orange-red) and the (Tb3+) chelates at ~548 millimicrons (yellow-green).

Figure 5:
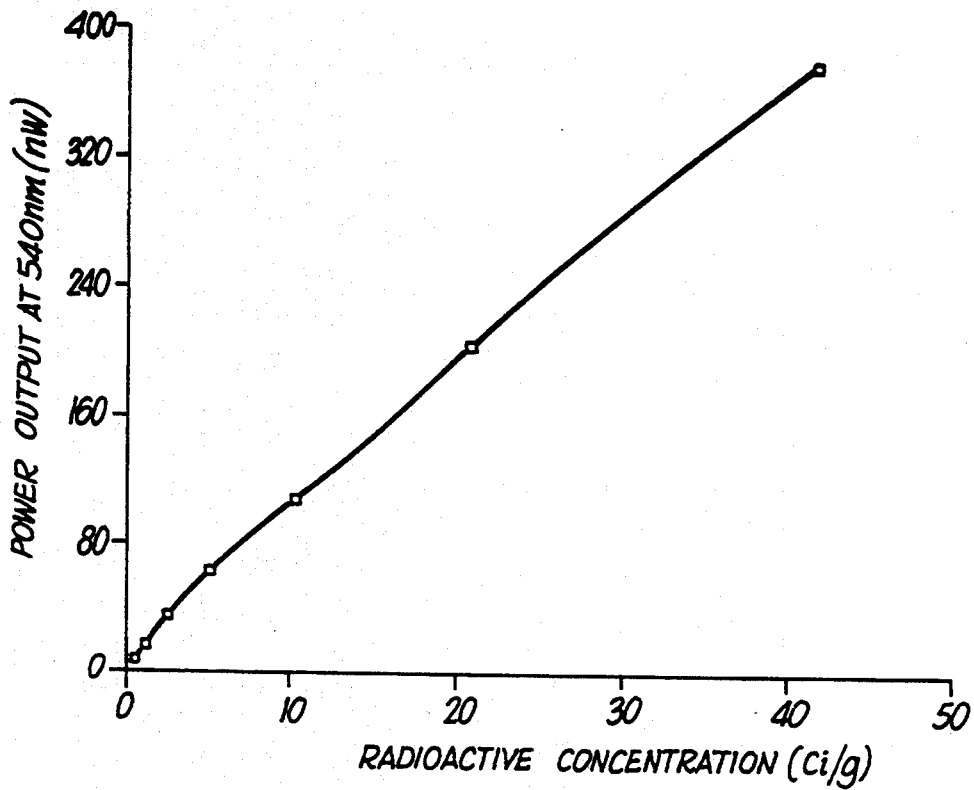
FIG. 5 is a graph of power output against radioactive concentration.

FIG. 5 is a graph of power output at 540 nm (expressed in nW) against radioactive concentration (Ci/g) of the polymer in 3 MB Microtec gas cells. The phosphor concentration was held constant at 120 mg/ml. The power output goes up more or less linearly with increasing radioactive polymer concentration. At the higher concentrations shown, the polystyrene would have had a limited life due to radiation damage.

EXAMPLE 6

Figure 7:
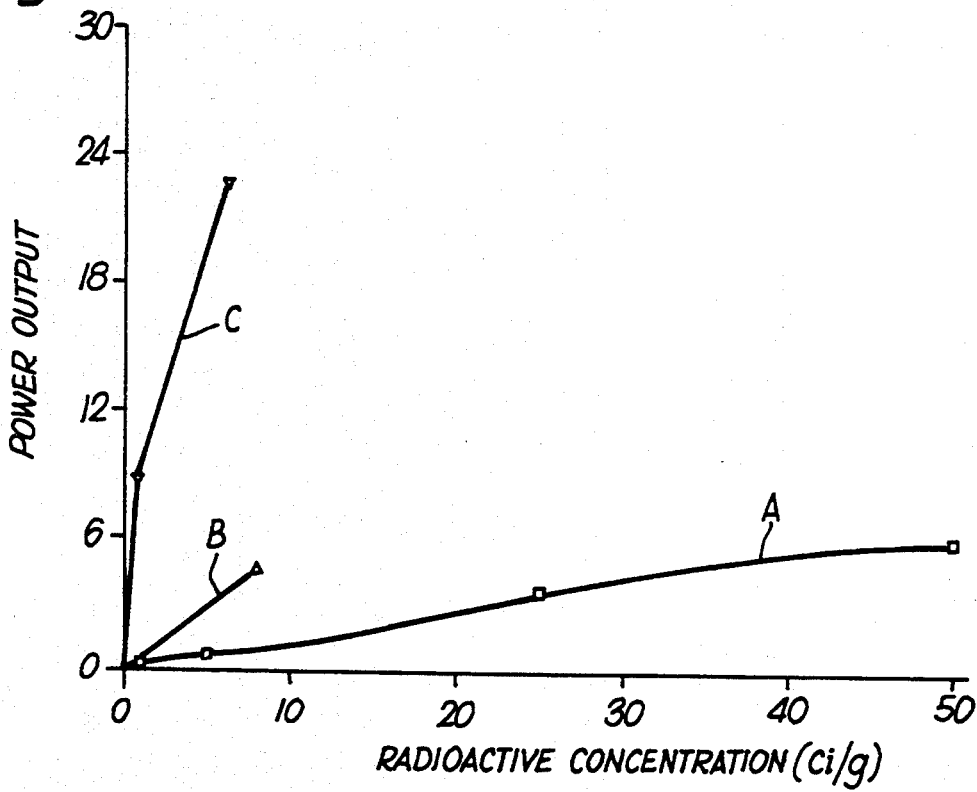
FIG. 7 is a graph comparing efficiencies in terms of power output, of various light emitting sources.

FIG. 7 is a graph comparing efficiencies of various different light emitting sources, expressed as power output (nW) against polymer radioactive concentration (Ci/g). In this graph:

Squares (line A) represent polymer sources as described in GB 2242908A.

Erect triangles (line B) represent the formulation of Example 5b).

Inverted triangles (line C) represent formulations according to Example 2 containing a phosphor concentration of 120-150 mg/ml of polymer The diamond represents a commercially available source comprising tritium gas contained in a glass vessel coated with a zinc sulphide scintillant.

Figure 8:
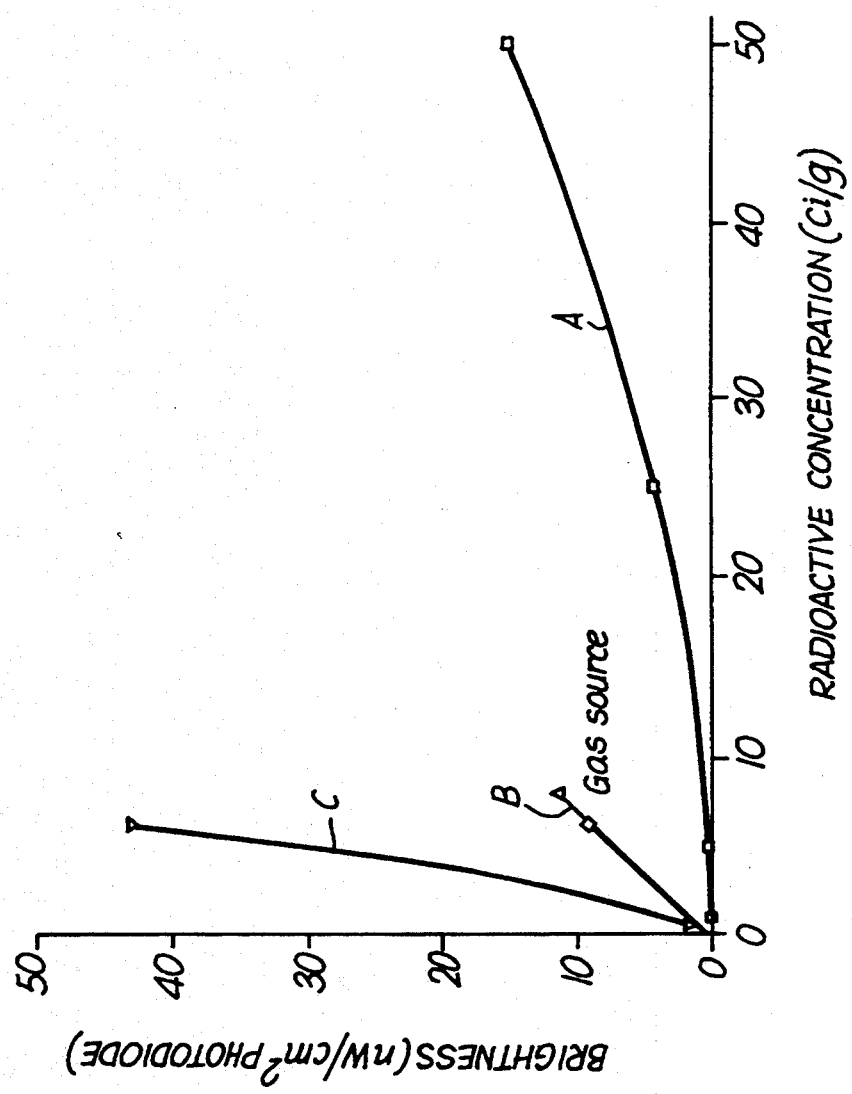
FIG. 8 is a graph comparing efficiencies, in terms of brightness, of the same light emitting sources.

FIG. 8 is a comparable graph, in which the ordinate is not power output but brightness expressed in nW/cm$^2$ of photodiode. Performance of the Example 5b) formulation (B) is strikingly superior to that of the previously known polymer sources (A). Performance of the formulations (C) according to Example 2 is strikingly superior to the performance of all other sources including the commercially available gas source.

EXAMPLE 7

Tris(dibenzoylmethide)bis(diphenyl-phosphonimido-triphenyl phosphorane) europium III (EuIII[DBM]$_3$[DPTP]$_2$)

A. Preparation of europium III tris(dibenzoylmethide) (EuIII [DBM]$_3$

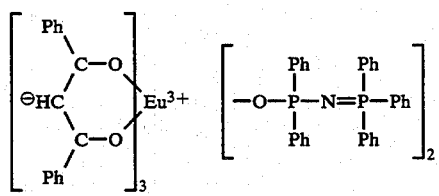

Dibenzoyl methane, 100 mmoles, 22.43 grams, (ex Aldrich Chemical Co. Ltd.), m.p. 77.5°-79° C.), and sodium hydroxide 100 mmoles, 4 grams, were reacted together in 50% v/v ethanol:water, 200 ml at room temperature to give a solution of the sodium salt of dibenzoyl methide at a concentration of 0.5 millimoles/ml.

Europium III chloride hexahydrate m.wt. 366.31, 6 millimoles 2.2 grams (ex Aldrich Chemical Co.), was dissolved in 50 ml 50% v/v ethanol:water at c.60° C., and to this was added with stirring 18 millimoles, 36 ml of the solution of sodium dibenzoyl methide prepared as above.

The EuIII[DBM]$_3$ monohydrate precipitates out, is filtered off, washed with water and dried.

B. Preparation of (EuIII[DBM]$_3$[DpTp]$_2$)

EuIII[DBM]$_3$ monohydrate m.wt. 839.74, 2 millimoles, 1.68 grams and diphenyl-phosphonimidotriphenyl phosphorane m.wt. 477.45, 4 millimoles, 1.91 grams are melted together at 200° C. in an oven and held at that temperature for one hour. The product is then dissolved in hot toluene 15 milliliters and added carefully to cold stirred trimethyl pentane, 500 milliliters, to precipitate the complex which is filtered off, dried and weighed, yield 3.1 grains, 86% of theory of 3.59 grams, m.wt. 1776.64.

C. Comparison of fluorescent properties of europium III tris(dibenzoyl methide) and its bis(diphenyl phosphonimido-triphenyl phosphorane) derivative prepared as above and incorporated into polystyrene EuIII[DBM]$_3$, 30 mg was dissolved in 1 ml styrene, polymerised using 1.25 mg AZBN, heating overnight at 75° C., and shaped into a flat sheet ~1.5 mm thick. Surface reflectance measurements were made at room temperature and at approx. −140° C. using an excitation wavelength of 360 nm. EuIII[DBM]$_3$[DPTP]$_2$ 25 mg was similarly treated and measured.

The measurements showed that, without any adjustment for concentration, the fluorescence from EuIII[DBM]$_3$[DPTP]$_2$ in polystyrene was approximately 6.66 times more intense than that of EuIII[DBM]$_3$.

If allowance were to be made for molar concentration then the ratio was 17.29.

The comparisons of the emissions at room temperature and approx. −140° C. of the same sample is thought to compare the size of the energy population of the triplet level (measurement at −140° C.) with the size of the fluorescence emission (at RT) thereby indicating the efficiency with which that energy has been transferred to the lanthanide ion and emitted. On this basis:

EuIII[DBM]$_3$ shows an efficiency of 36%.

EuIII[DBM]$_3$[DPTP]$_2$ shows an efficiency of 79.72%. i.e. a 2.2 fold increase in efficiency.

The corresponding Samarium III chelates, namely SmIII[DBM]$_3$[DpTp]$_2$ and SmIII[DBM]$_3$[DPTP] have also been made and tested; the former of these two shows good fluorescence properties, the latter also fluoresces in polystyrene.

EXAMPLE 8

Various analogues of styrene were investigated as potential light emitting polymer matrices.

The monomers were polymerised (as described in Example 2) with a fixed amount of compound (1) (Example 1) hereinafter called ALP-1 at fixed radioactive concentration. The radioactivity was introduced by 'spiking' the monomer with small quantities of tritiated styrene (<10% v/v). The results are shown in Table 1.

TABLE 1
Relative light Output of Some Styrene Analogues

| Styrene Analogue | Relative Light Outputs (Arbitrary Units) |
|---|---|
| Styrene | 100 |
| 4-t-Butylstyrene | 106 |
| 4-Methylstyrene | 97 |
| 2,4-Dimethylstyrene | 88 |
| 4-Methoxystyrene | 60 |
| 2,4,6-Trimethylstyrene | 39 |
| 4-Vinyl-biphenyl | 65 |

Polymerisations carried out at 100° C. t-butyl peroxide initiator (1.5% w/v), 10% ALP w/v.

EXAMPLE 9

Some 1,3-diketonates of terbium are shown in Table 2. Compounds (1) and (2) are available through commercial suppliers. Compound (3) is a novel fluorescent chelate based on the ligand imidotetraphenyldiphosphinic acid (5). Their relative light outputs in tritiated polystyrene are shown in Table 2.

The relative light outputs were determined using a standard luminometer with 2% w/v fluor in tritiated styrene at 100 μCi/ml. Polymerisation carried out at 100° C. with t-butylperoxide initiator.

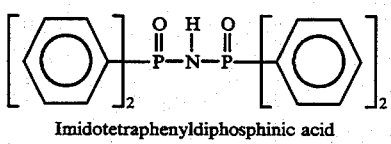

Imidotetraphenyldiphosphinic acid (5)

EXAMPLE 10

Example 1 describes the compound ALP-1 which contains a Lewis base adduct in the form of diphenylphosphonimido triphenylphosphorane. This compound confers high solubility in styrene and high fluorescence efficiency on tris(2,2,6,6-tetramethyl-3,5-heptanedionato) terbium (III) when adducted. Therefore, work was undertaken to vary the functionality of this phosphorane compound to investigate structure/fluorescence efficiency relationships when adducted to terbium chelates. The relative light outputs were determined using a standard luminometer with 1 mmol/ml fluor in tritiated styrene

TABLE 2
Relative Light Output of Some Terbium 1,3-Diketonate Chelates

| Chelate | Compound Number | Relative Light Output (Arbitary units) |
|---|---|---|
| (structure shown) | (1) | 25 |
| (structure shown) | (2) | 50 |
| (structure shown) | (3) | 10 |
| ALP-1 | (4) | 100 | at 100 μCi/ml, polymerisation carried out at 100° C. with t-butylperoxide initiator. The results are shown in Table 3. All the compounds shown in Table 3 were also incorporated in high radioactive concentration polystyrene, and showed the characteristic green emission of terbium fluorescence displayed by ALP-I.

EXAMPLE 11

A more general investigation of other Lewis base adducts was carried out. Adducts of tris(2,2,6,6-tetramethyl-3,5-heptanedionato)terbium (III) were prepared in situ during polymerisation. The relative light outputs were determined using a standard luminometer with chelate:Lewis base (1:1) at 1 mmol/ml in styrene at 100 μCi/ml. Polymerised at 100° C. with t-butylperoxide initiator. The results are shown in Table 4.

EXAMPLE 12

A polymerisable phosphine oxide, p-styryldiphenyl phosphine oxide (12) was prepared and its adduct with tris(2,2,6,6-tetramethyl-3,5-heptanedionato)terbium (III) prepared in situ as described. Results were obtained for various fluor loadings and were shown to be essentially the same (up to a fluor concentration of 5% w/v) as for triphenyl phosphine oxide.

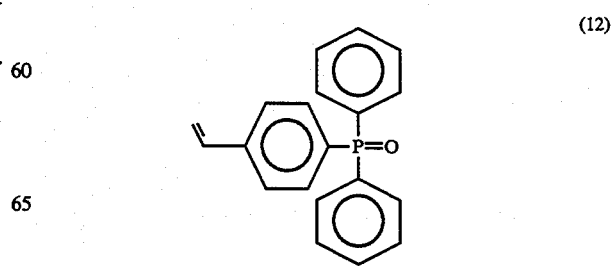

(12)

TABLE 3

Relative Light Outputs of Various Phosphorane Adducts of Tris (2,2,6,6-tetramethyl-3,5-heptanedionato)terbium (III)

| Phosphorane Adduct | Compound Number | Relative Light Output (Arbitrary units) |
|---|---|---|
| [Ph₂P=N—PPh₂=O structure] | (4) | 100 |
| [tri-(t-butylphenyl)-phosphoranyl structure] | (6) | 83 |
| [tri-(pyridyl)-phosphoranyl structure] | (7) | 64 |
| [Ph₃As=N—P(=O)Ph₂ structure] | (8) | 64 |
| [(PhO)₂P(=O)—N=P(=O)(OPh)₂ structure] | (9) | 50 |

TABLE 3-continued

Relative Light Outputs of Various Phosphorane Adducts of Tris (2,2,6,6-tetramethyl-3,5-heptanedionato)terbium (III)

| Phosphorane Adduct | Compound Number | Relative Light Output (Arbitrary units) |
|---|---|---|
| [Ph₃P=O structure] | (10) | 98 |
| (n-C8H17)3P=O | (11) | 82 |

TABLE 4

Lewis Base Adducts of Tris(2,2,6,6-tetramethyl-3,5-heptanedionato)terbium(III)

| Lewis Base Adduct | Relative Light Output (Arbitrary units) |
|---|---|
| No Adduct | 25 |
| Diphenylphosphonimido-triphenylposphorane | 100 |
| Tri-n-octylphosphine oxide | 52 |
| Triphenylphosphine oxide | 98 |
| Triphenyl arsyl oxide | 19 |
| Tributyl phosphate | 15 |
| Triphenylphosphate | 42 |
| N,N-Dimethylformamide | 37 |
| Morpholine | 30 |
| Piperidine | 45 |
| Pyridine | 29 |
| 4-Vinyl-Pyridine | 23 |
| Dimethylsulphoxide | 42 |
| Bipyridyl | 7 |

EXAMPLE 13

Tetrakis(2,2,6,6-tetramethyl-3,5-heptanedionato)terbium (III), piperidine salt (13) was prepared, its relative light output was determined to be half that of ALP-1 when incorporated in a tritiated polystyrene matrix. Determined by a standard luminometer at 100 μCi/ml, polymerised at 100° C. with t-butylperoxide catalyst.

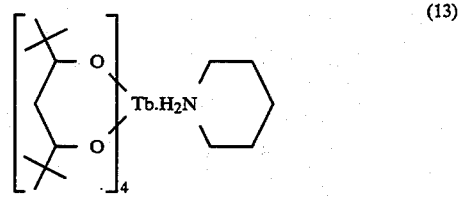

(13)

EXAMPLE 14

Many of the Examples are based on efficient terbium fluors. In the lanthanide series however, europium, samarium and dysprosium also show useful ion fluorescence.

Terbium and europium in general are reported as more efficient than samarium and dysprosium. For europium, some extremely efficient perfluorinated 1,3-diketonate chelates are described in the literature, naphthoyl trifluoro acetone for example. These compounds normally produce a deep red fluorescence. However, when these fluorine containing compounds are incorporated in a tritiated polymer matrix at >1 Ci/ml rapid radioactive degradation ensues, resulting in loss of light output.

Figure 9:
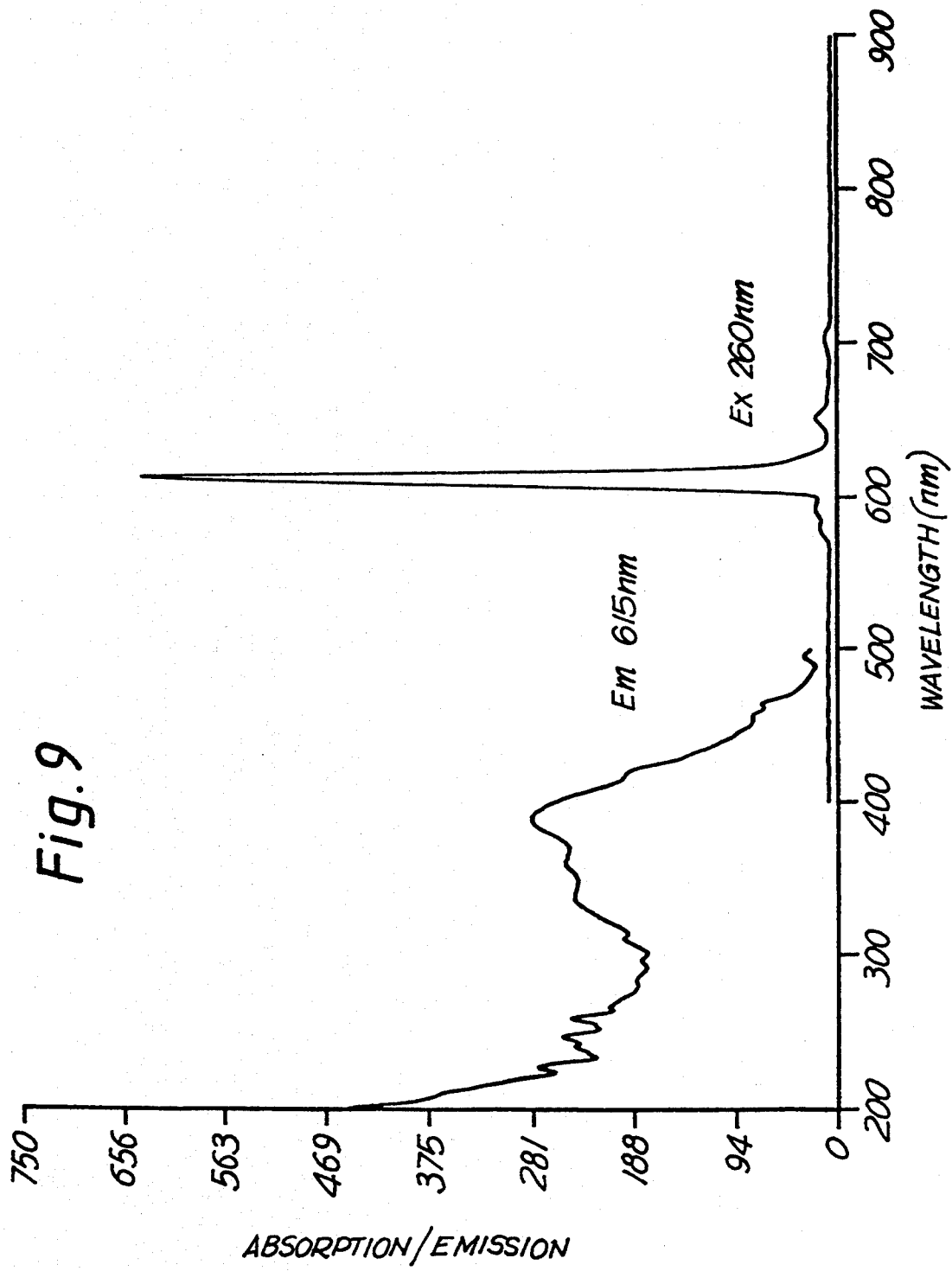
FIGS. 9 to 12 represent graphs of the excitation/emission spectra of various compounds of the instant invention.
Figure 10:
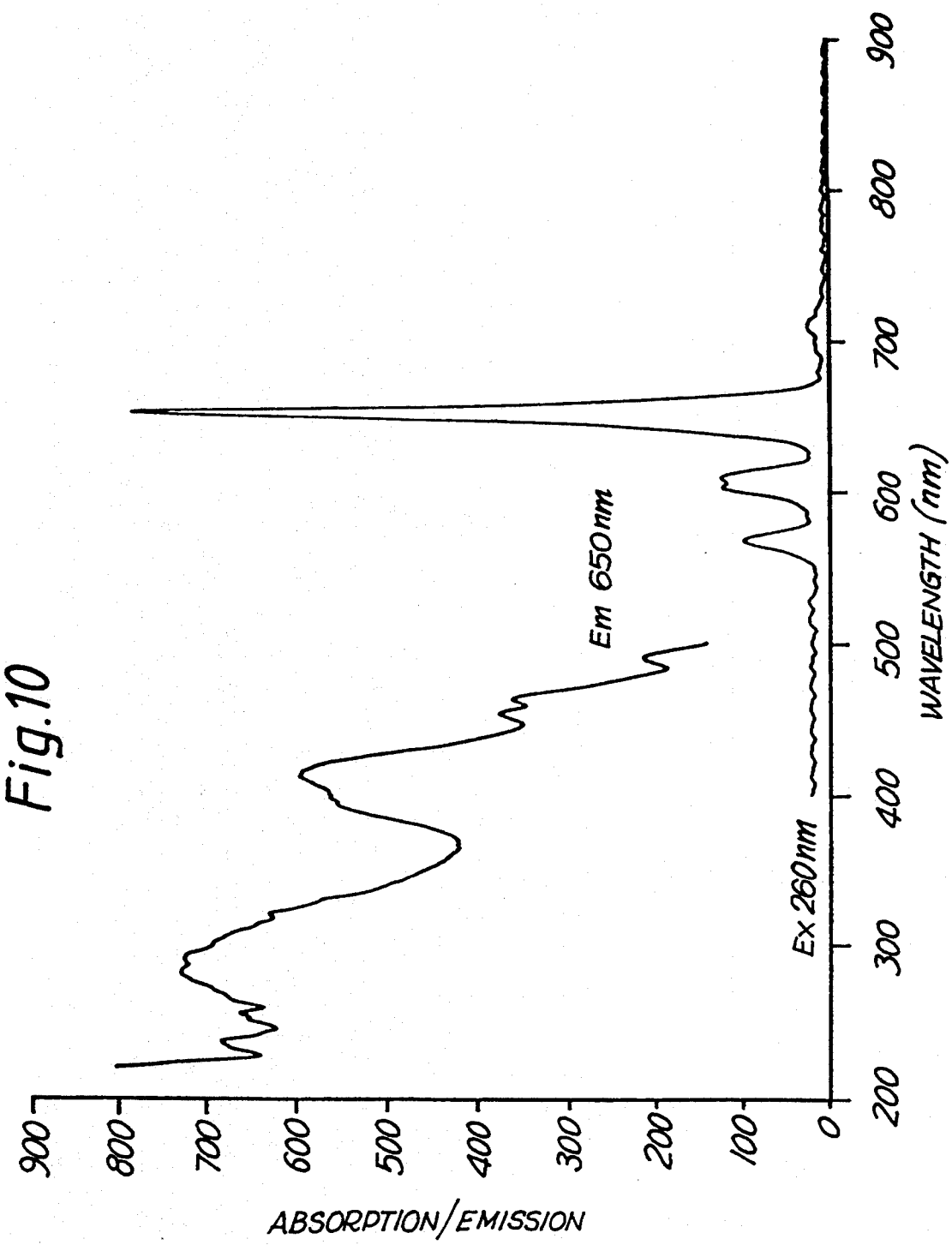

However, the known tris-(dibenzoylmethide) chelates of europium and samarium prove to be stable and moderately efficient fluors when incorporated in tritiated polystyrene. Both chelates are rendered more stable and more efficient as fluors when adducted with diphenylphosphonimido triphenylphosphorane to give compounds (14) and (15). Their excitation/emission spectra as shown in FIGS. 9 and 10. Thus, FIG. 9 depicts excitation/emission spectra of Tris(dibenzoylmethide) europium (III) Diphenylphosphonimido triphenylphosphorane, and FIG. 10 depicts excitation/emission spectra of Tris(Dibenzoylmethide)samarium-(III) Diphenylphosphonimido triphenylphosphorane.

Figure 11:
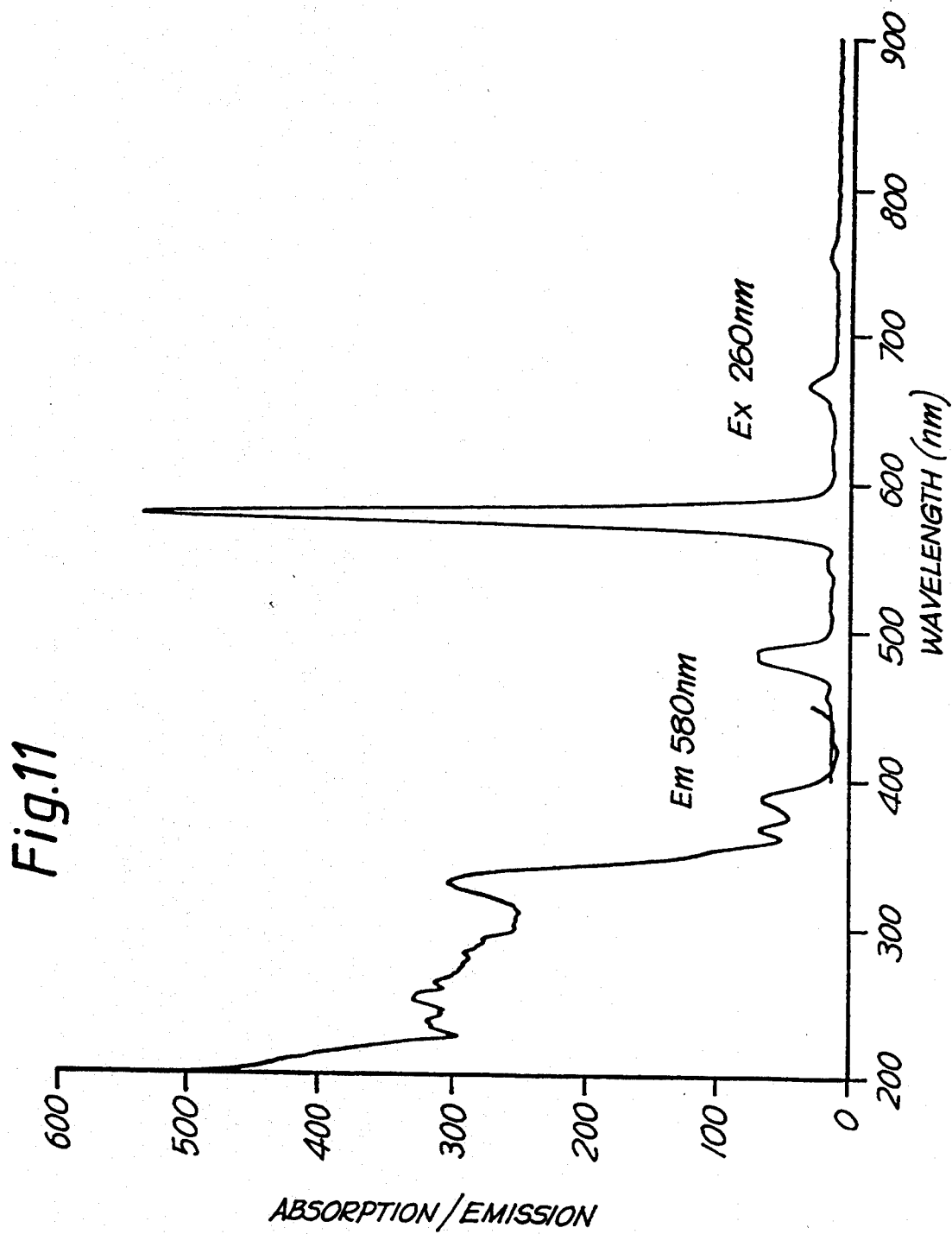

Tris (2,2,6,6-tetramethyl-3,5-heptanedionato)dysprosium (III) and its diphenylphosphonimido triphenylphosphorane adduct (16) have been prepared, both fluoresce yellow under UV irradiation. Compound (16) also gives the same emission when incorporated in tritiated polystyrene (5 Ci/g). Its excitation/emission spectra is shown in FIG. 11.

EXAMPLE 15

Figure 12:
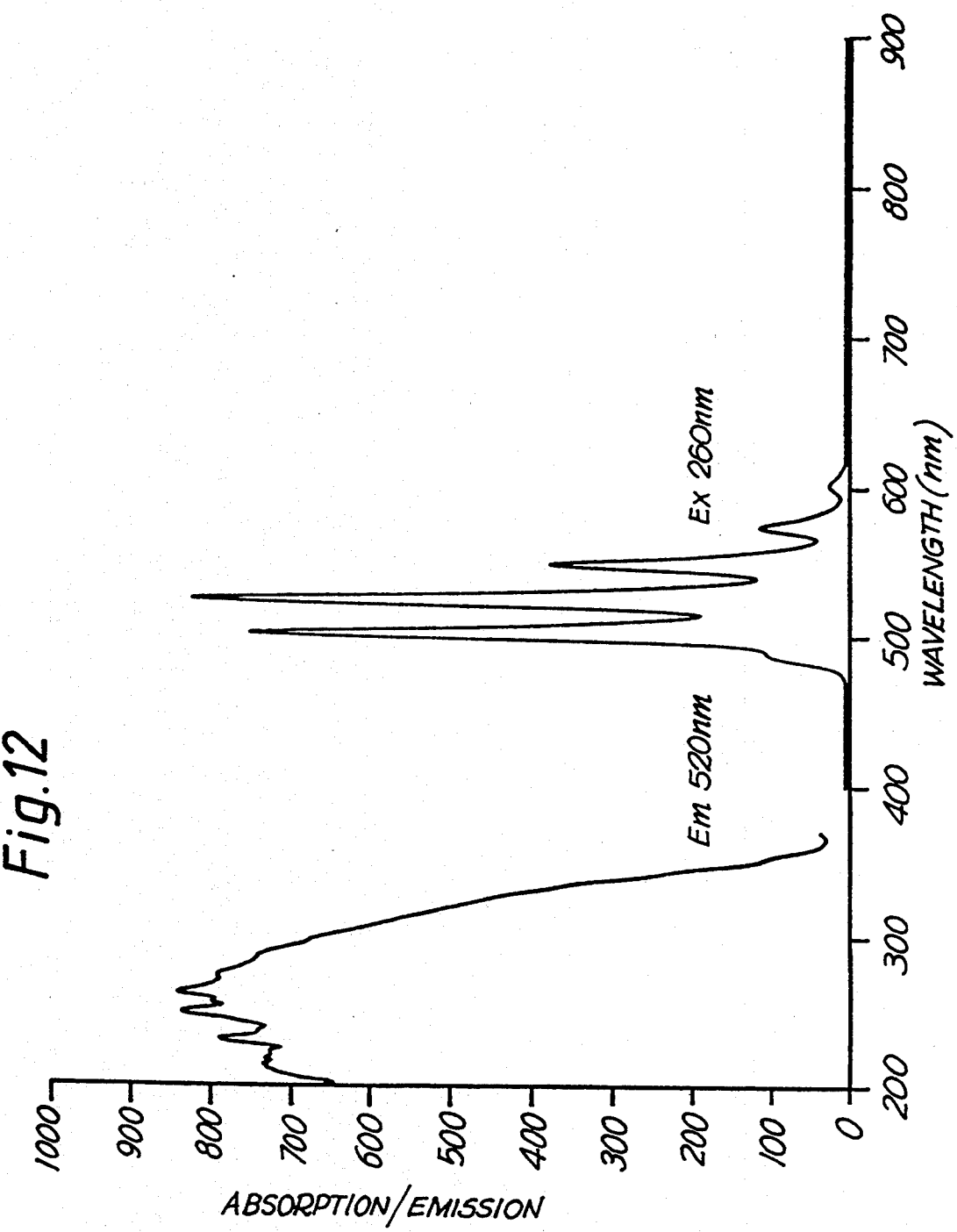

Of the actinides uranium as its dioxide has been investigated. The chelate shown below (17) fluoresces green under UV irradiation and when incorporated in tritiated polystyrene. Adduction of this compound with diphenylphosphonimido triphenyl phosphorane increases the solubility of the chelate in styrene. This is a new type of fluorescent uranyl chelate. We are unaware as yet, of any other room temperature fluorescent uranyl chelate of this type. Its excitation/emission spectra is shown in FIG. 12. Thus, FIG. 12 depicts excitation/emission spectra of Bis(imidotetraphenyldiphosphinic acid)uranium dioxide(II).

EXAMPLE 16

Waveshifters such as dimethyl-POPOP and xylene may be incorporated in tritiated polystyrene with ALP-1 to increase the light output (10–20%) with various loadings 1–10% w/v waveshifter.

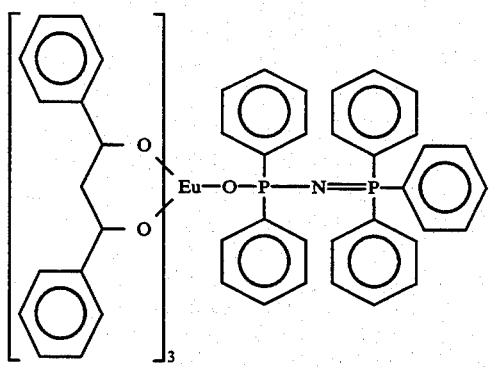

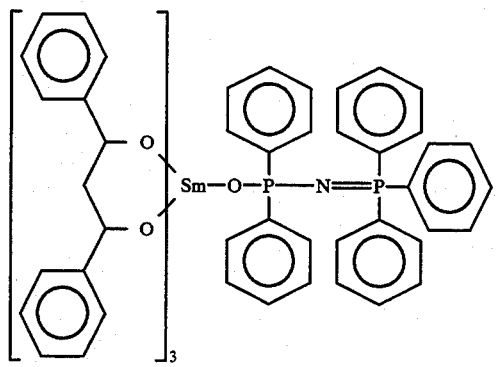

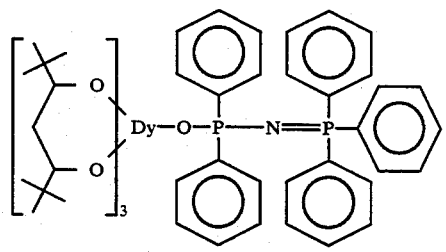

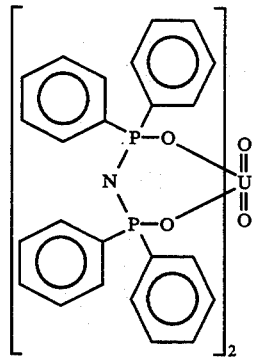

Experimental: General

Unless stated otherwise the chemicals used in this work were obtained through commercial sources and were used without further purification. H.p.l.c. grade solvents were used wherever possible, for reactions involving moisture sensitive reagents, Aldrich sure-seal dry solvents were used. Synthetic procedures have already been described in the preliminary patent application for ALP-1 and diphenylphosphinyl azide (a commonly used reagent).

Melting points were obtained on a Seiko DSC 220 differential scanning calorimeter. Excitation/emission spectra were recorded on a Perkin Elmer LS-50 spectrofluorimeter.

Preparation of Tris(Imidotetraphenyldiphosphinic acid)terbium(III) (3)

Bis(diphenylphosphino)imine

Diphenylphosphinylchloride(57.5 g, 0.261 mole) in toluene (100 ml) was added to hexamethyldisilazane (21.0 g, 0.130 mole) in toluene (50 ml) at 80°–90° C. over 20 minutes. The reaction mixture was heated at 85° C. for 2 hours then 100° C. for 1 hour. The reaction mixture was then evaporated to Ca 100 ml volume. A white solid was collected upon cooling. Recrystallization from hot toluene gave a white solid 19.5 g. (top 147° C.; Lit[2] mp. 149–151).

Imidotetraphenyldiphosphinic acid (5)

Hydrogen peroxide (6 ml, 30% w/v) was added dropwise to a suspension of bis(diphenylphosine)imine (10 g, 26 mmole) in tetrahydrofuran (100 ml) at 5° C. The reaction mixture was stirred for two hours and then filtered. The solid was dissolved in methanol:ammonia (4:1; 25 ml), the solution filtered, then acidified with concentrated hydrochloric acid, a solid precipitated which was washed with water (30 ml), ethanol (30ml) and hexane (30 ml) to give a white solid (8.6 g). (mp. 279° C. lit;[2] m.p. 283° C.).

Tris(Imidotetraphenyldiphosphinic acid)terbium(III)(3)

Imidotetraphenyldiphosphinic acid (8.34 g, 20 mmole) and potassium hydroxide (1.12 g, 20 mmole) were heated to reflux in ethanol/water (10:3, 130 ml) for 10 minutes. A fine precipitate was filtered off.

Terbium chloride (hexahydrate) (2.48 g, 6.64 mmole) in ethanol water (5:2, 35 ml) was added to the hot reaction solution over 25 minutes.

The reaction mixture was then heated to reflux for 30 minutes. The reaction mixture was cooled, filtered and washed with water (50 ml) and ethanol (50 ml). The product was dried under vacuum at 90° C. for two hours to give the product as an amorphous white powder (7.2 g). (mp. 280° C. dissoc.).

Compounds 6, 7, 8 and 9 were prepared by the same general method as that described for Compound 4.

Preparation of
Tris(2,2,6,6-tetramethyl-3,5-heptanedionato)terbium-(III)-triphenylphosphine oxide(10)

Tris(2,2,6,6-tetramethyl-3,5-heptanedionato)terbium (III) (14.17 g, 0.02 moles) and triphenylphosphine oxide (5.57 g, 0.02 moles) were refluxed in trimethylpentane (150 ml) for 30 minutes. The reaction mixture was cooled with stirring in an ice/bath. The mother liquor was decanted and the product dried under vacuum to give the product as a white crystalline solid (17.2 g) (mp. 148° C.).

Preparation of
Tris(2,2,6,6-tetramethyl-3,5-heptanedionato)terbium-(III)-tri-n-octylphosphineoxide(11)

Tris(2,2,6,6-tetramethyl-3,5-heptanedionato)terbium-(III) (5.0 g, 7.1 mmole) and tri-n-octylphosphine oxide (2.75 g, 7.1 mmole) were refluxed in trimethylpentane (50 ml) for 2 hours. The solvent was evaporated to give the product as an amber oil (7.6 g).

Preparation of p-Styryldiphenylphosphine oxide(12)

p-Styryldiphenylphosphine p-Styryldiphenylphosphine was prepared according to published procedure[6]. P-Chlorostyrene (30.0 g, 0.22 m) in tetrahydrofuran (100 ml) was added to magnesium turnings (15 g) at such a rate as to maintain reflux. The reaction was initiated by adding 3 ml ethyl bromide to the magnesium turnings. After 30 minutes, the reaction mixtures cooled to room temperature and was stirred for an additional 30 minutes. The reaction solution was then added slowly to chlorodiphenylphosphine (40.4 g, 0.183 m) in tetrahydrofuran (100 ml) with ice-bath cooling. The reaction mixture was stirred for 1 hour and then poured onto 3 m ammonium chloride solution (300 ml). The organic layer was then separated, dried over anhydrous sodium sulphate and filtered. Polymeric material was precipitated from solution by adding hexane (500 ml). The solution was then filtered and evaporated to give the product as a white amorphic solid which was crystallised from methanol as white crystals (18.0 g).

p-Styryldiphenylphosphine oxide (12)

Hydrogen peroxide (30% w/v, 7 ml) was added dropwise to styryldiphenylphosphine (8.4 g, 29.2 mmole) in tetrahydrofuran (100 ml) at 5° C. over 30 minutes. The reaction mixture was then stirred at room temperature for 2 hours. The solvent was then evaporated and the product dried under vacuum at room temperature to give a clear oil (8.8 g).

Preparation of
Tetrakis(2,2,6,6-tetramethyl-3,5-heptanedionato)terbium(III) piperidine salt (13)

2,2,6,6-tetramethyl-3,5-heptanedione (0.92 h, 5 mmole) and piperidine (0.43 g, 5 mmole) were heated at 70° C. in ethanol (30 ml) for 20 minutes. Terbium chloride (0.27 g, 1 mmole) in ethanol (10 ml) was then added and the reaction mixture heated at 70° C. for 2 hours. The product was allowed to crystallize overnight at room temperature and then isolated by filtration as a white solid (mp. 110° C., decomp.).

Preparation of Tris(dibenzolylmethide)europium(III) diphenyl-phosphonimido triphenylphosphorane(14)

Tris(dibenzoylmethide)europium(III)

Europium chloride hexahydrate (2.2 g, 6.0 mmole) in 50% aqueous ethanol (50 ml) was added to a solution of the sodium salt of dibenzoylmethide (4.37 g, 18 mmole) in aqueous ethanol (35 ml) at 60° C. The reaction was stirred at 60° C. for 30 minutes, then cooled, filtered and the solid collected, washed with water (50 ml) and dried to give the product as a bright yellow solid (4.5 g).

Tris(dibenzolylmethide)europium(III) diphenyl-phosphonimido triphenylphosphorane(14)

Tris(dibenzoylmethide)europium(III) (3.6 g, 4.2 mmole) and diphenylphosphonimido triphenylphosphorane (2.0 g, 4.2 mmole) were refluxed in trimethylpentane (50 ml) for 30 minutes. Reaction mixture filtered wash with pentane (30 ml) to give the product as a yellow solid (5.0 g).

Preparation of
Tris(dibenzoylmethide)samarium(III)diphenylphosphonimido triphenylphosphorane(15)

Tris(dibenzoylmethide)samarium(III)

Samarium chloride anhydrous (2.56 g, 10 mmole) in 50% aqueous ethanol (50 ml) was added to a solution of the sodium salt of dibenzoylmethide (6.69 g, 30 mmole) in 50% aqueous ethanol (60 ml) at 60° C. The reaction mixture was stirred at this temperature for 30 minutes. The reaction mixture was then cooled, filtered and the solid washed with water (50 ml) to give a bright yellow amorphous solid (7.9 g).

Tris(dibenzoylmethide)samarium(III)diphenylphosphonimido triphenylphosphorane(15)

Tris(dibenzoylmethide)samarium(III) (1.5 g, 1.83 mmole) and diphenylphosphonimido triphenylphosphorane (0.87 g, 1.83 mmole) were refluxed in trimethylpentane (30 ml) for 30 minutes. The reaction mixture was cooled, filtered and the product dried under vacuum for 2 hours to give a yellow amorphous solid (2.0 g) (mp. 163° C.).

Preparation of Tris(2,2,6,6-tetramethyl-3,5-heptanedionato)dysprosium(III)diphenylphosphonimido triphenylphosphorane(16)

Tris(2,2,6,6-tetramethyl-3,5-heptanedionato)dysprosium(III) (6.1 g, 9.75 mmole) and diphenylphosphonimido triphenyphosphorane ** were refluxed in trimethylpentane (60 ml) for 30 minutes. The mother liquor was decanted from a small amount of insoluble material and allowed to cool to room temperature. A white crystalline material formed which was redissolved in diethyl ether (70 ml) and clarified by filtration through a 0.45 micron filter. The solvent was evaporated to give a white solid (8.1 g, mp. 154° C.).

Preparation of Bis(Imidotetraphenyldiphosphinic acid)Uranium dioxide. (II)(17)

Imidotetraphenyldiphosphinic acid (4.30 g, 10.3 mmole) and sodium hydroxide (0.412 g, 10.3 mmole) were heated to 60° C. in 90% aqueous ethanol (100 ml). Uranyl acetate (2.0 g, 5.15 mmole) in 50% aqueous ethanol (40 ml) was then added quickly and the reaction mixture hated to reflux for 20 minutes. The reaction mixture was cooled to room temperature, filtered, washed with ethanol (30 ml) and dried under vacuum to give the product as a yellow solid (4.4 g).

We claim:

1. A compound that results from reacting together an imido-reactant of the formula

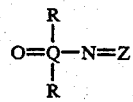

where Q is P or As,
R is aromatic or heterocyclic, and Z is $QR_3$ or an oligophosphoranyl group, with a chelate of a lanthanide or actinide metal ion selected from the group consisting of Tb, Eu, Sm, Dy, U and $UO_2$ to produce a product which has the property of fluorescing in UV radiation.

2. The compound as claimed in claim 1, having the formula

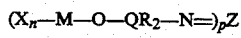

or

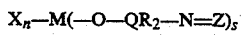

where M is the lanthanide or actinide metal ion,
X is a chelating group,
n is 1 to 4,
p is 1 to 4, and
s is 1 to 4.

3. The compound as claimed in claim 1, wherein the imido-reactant has the formula

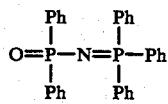

where Ph is phenyl.

4. The compound as claimed in claim 1, wherein the chelate comprises a chelating moiety of the formula

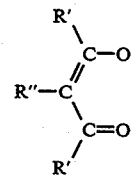

wherein R' is aromatic or heterocyclic, and R" is aromatic, heterocyclic or hydrogen.

5. The compound as claimed in claim 4, wherein R' is t-butyl and R" is hydrogen.

6. The compound as claimed in claim 4, wherein R' is phenyl and R" is hydrogen.

7. The compound as claimed in claim 6, wherein the metal ion is europium 3+.

8. The compound as claimed in claim 7 which is tris(dibenzoylmethide) bis(diphenylphosphonimidotriphenylphosphorane) europium III having the structure:

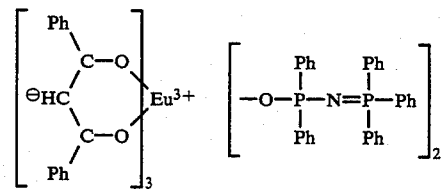

9. The compound as claimed in claim 5, wherein the metal ion is terbium 3+.

10. A compound that results from reacting an imido-reactant of formula

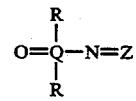

where Q is P or As,
one of the R substituents is a copolymerizable group, while
the other R substituent is aromatic or heterocyclic,
and Z is $QR_3$ or an oligophosphoranyl group, with a chelate of a lanthanide or actinide metal ion selected from the group consisting of Tb, Eu, Sm, Dy, U and $UO_2$ to produce a product which has the property of fluorescing in UV radiation.

11. The compound as claimed in claim 10, having the formula

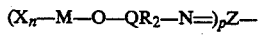

or

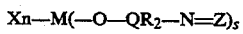

where M is a lanthanide or actinide metal ion,
X is a chelating group,
n is 1 to 4,
p is 1 to 4, and
s is 1 to 4.

12. A compound that results from reacting an imido-reactant of formula

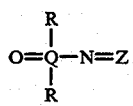

where Q is P or As,
one of the R substituents is a copolymerizable group, while
the other R substituent is aromatic or heterocyclic, and Z is $QR_3$ or an oligophosphoranyl group, with a chelate of a lanthanide or actinide metal ion selected from the group consisting of Tb, Eu, Sm, Dy, U and $UO_2$ to produce a product which has the property of fluorescing in UV radiation; wherein the chelate comprises a chelating moiety of the formula

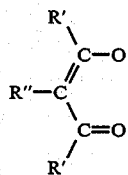

where each R' is a hydrocarbon or fluorocarbon, and R" is fluorocarbon, hydrocarbon or hydrogen.

13. The compound as claimed in claim 12, having the formula

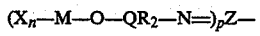

$(X_n-M-O-QR_2-N=)_pZ-$ or

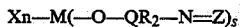

$X_n-M(-O-QR_2-N=Z)_s$ where M is the lanthanide or actinide metal ion,
X is a chelating group,
n is 1 to 4,
p is 1 to 4, and
s is 1 to 4.

14. A solid body comprising an organic polymer together with a compound according to claim 1, the body being capable of emitting light when subjected to a flux of electromagnetic radiation.

15. A solid body which is transparent or translucent, comprising an organic polymer together with the compound of claim 1, wherein the body is radioactively labelled with tritium, the body having the property of emitting light by virtue of internally generated ionizing radiation resulting from radioactive decay of the tritium.

16. The body as claimed in claim 15, wherein the chelate comprises a chelating moiety of the formula

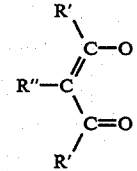

wherein R' is aromatic or heterocyclic, and R" is aromatic, heterocyclic or hydrogen.

17. The body as claimed in claim 16, wherein R' is t-butyl or phenyl and R" is hydrogen.

18. A body as claimed in claim 15, wherein the chelate is europium (3+)(naphthalene trifluoroacetyl acetonate)$_4$ bipyridyl.

19. The body as claimed in claim 15, wherein the chelate is terbium (3+) (pivaloylmethide)$_3$ tripyrazolyl borate.

20. The body as claimed in claim 15, wherein the polymer is radioactively labelled with tritium.

21. The body as claimed in claim 20, wherein the polymer is labelled with tritium to an activity of 1 $\mu$Ci/g to 100 Ci/g.

22. The body as claimed in claim 15, wherein the polymer is thermoplastic.

23. The body as claimed in claim 15, wherein the organic polymer is a poly(vinylaromatic) hydrocarbon.

24. The body as claimed in claim 15, which has been formed by subjecting to polymerization conditions a reaction mixture comprising at least one polymerizable monomer and at least one chelate of a lanthanide or actinide metal.

25. The body as claimed in claim 24, wherein at least one polymerizable monomer is tritiated.

26. The body as claimed in claim 15, in the shape of a cylinder with the curved surface made internally reflecting, or of a chord of a cylinder with the curved surface and the ends made internally reflecting.

27. The body is as claimed in claim 15, wherein some or all of the protium hydrogen in said polymer and/or in said at least one chelate of a transition or lanthanide or actinide metal is replaced by deuterium.

28. The body as claimed in claim 15, wherein at least one chelate of a lanthanide or actinide metal is present at a concentration of 1 $\mu$g to 250 mg per ml of polymer.

* * * * *